(12) United States Patent
Huang et al.

(10) Patent No.: US 8,644,693 B2
(45) Date of Patent: Feb. 4, 2014

(54) INTEGRATED MICROMACHINING PROXIMITY SWITCH SENSORS IN AIR/OIL LUBRICATORS

(75) Inventors: Liji Huang, San Jose, CA (US); Jiliang Ruan, Chengdu (CN); Jian Luo, Chengdu (CN); Chih-Chang Chen, Cupertino, CA (US)

(73) Assignee: Siargo Ltd., Santa Clara, CA (US)

( * ) Notice: Subject to any disclaimer, the term of this patent is extended or adjusted under 35 U.S.C. 154(b) by 894 days.

(21) Appl. No.: 12/796,565

(22) Filed: Jun. 8, 2010

(65) Prior Publication Data

US 2011/0301765 A1    Dec. 8, 2011

(51) Int. Cl.
*F24H 1/10* (2006.01)
(52) U.S. Cl.
USPC ................ 392/478; 392/314; 219/490
(58) Field of Classification Search
None
See application file for complete search history.

(56) References Cited

U.S. PATENT DOCUMENTS

| | | | |
|---|---|---|---|
| 7,233,000 B2 * | 6/2007 | Nassiopoulou et al. | ... 250/338.4 |
| 2005/0072926 A1 * | 4/2005 | Nassiopoulou et al. | ... 250/338.4 |
| 2008/0044939 A1 * | 2/2008 | Nassiopoulou et al. | ........ 438/54 |
| 2011/0301765 A1 * | 12/2011 | Huang et al. | .................. 700/282 |

* cited by examiner

*Primary Examiner* — Thor Campbell

(57) ABSTRACT

An apparatus integrated with micromachined (a.k.a. MEMS, Micro Electro Mechanical Systems) silicon thermal sensor as a proximity switch sensor in air/oil Lubricators is disclosed in the present invention. The present invention relates to mass flow sensing and measurement for both gas and liquid phase and relates to air/oil lubrication process for multi-point lubrication machine. The invented apparatus is utilized as an alarm device to prevent mechanical system failures caused by the discontinuity of oil lubrication. The MEMS silicon thermal sensor is distinguished with a variety of advantages of small size, low power consumption, high reliability and high accuracy. In addition to the above benefits, the most significant and critical advantage is its fast response time of less than 20 msec, which makes the proximity switch control become viable for preventing equipment damage from oil lubricants discontinuity.

3 Claims, 3 Drawing Sheets

INTEGRATED MICROMACHINING PROXIMITY SWITCH SENSORS IN AIR/OIL LUBRICATORS

FIELD OF THE INVENTION

Figure 1:
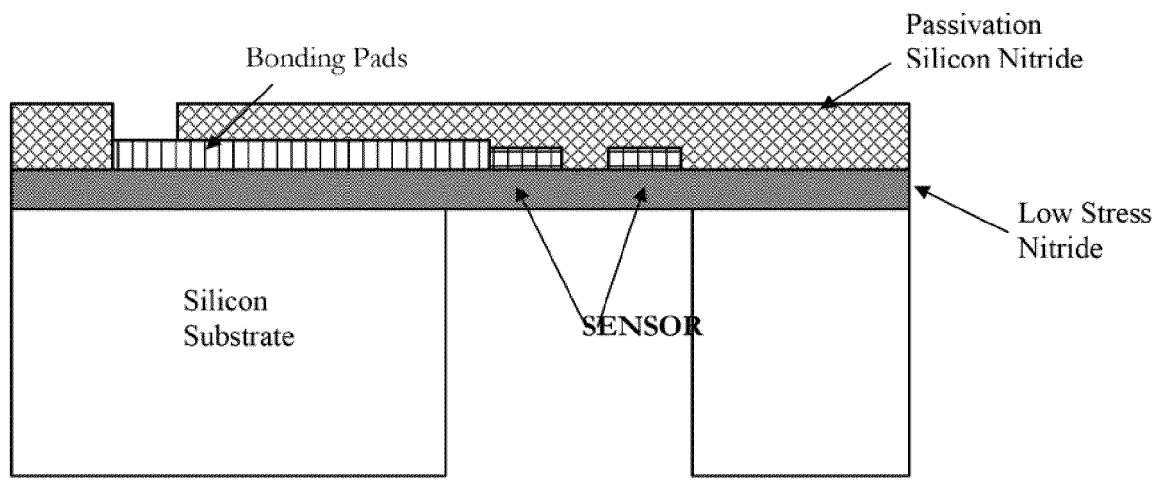

The embodiments of present invention are disclosed and written based on the application of a provisional patent (U.S. 61/220,298) which was previously filed on Jun. 25, 2009. The present invention relates to an apparatus which is functioning as a proximity switch sensor in air/oil lubricators system to detect the discontinuity of lubricant flow in mechanical systems by precisely measuring the thermal conductivity of flow media. To avoid the discontinuity of lubricants is very crucial and critical to the operation of many mechanical systems in various industrial applications. The apparatus of current invention is working as an alarm system for lubrication system to prevent mechanical equipment damages caused by lubricants dry-outs. The present invention also provides the methods and process for integrating with micromachining or Micro Electro Mechanical Systems (MEMS) thermal sensor into the proximity switch in air/oil lubricators.

BACKGROUND OF THE INVENTION

Air/oil lubricators or machines are new development in lubrication industry. It utilizes the high speed compressed air to carry the lubricant (oil) such that the lubricant will only travel along the tube or pipe walls in a form of a thin film. By properly controlling the air flow, the lubricant can be precisely delivered to the points where lubrication is required. This is to compare the prior oil mist lubricating technology that the compressed air impacts onto the lubricant making it into a misty formality and then the lubricant mist hits the lubricating points. Such a process is therefore neither environmentally friendly nor cost effective for lubricant. The new air/oil lubricating process separates the air and lubricant resulting in the air released after lubricating points will preserve its air composition whilst the lubricant can be precisely dosed. Hence the new process is environmental friendly and can save significant amount of lubricants. However, the new technology will require the precise control of the flow of the lubricant so that the discontinuity of the lubrication would not take place. The prior technology of proximity switch can monitor the lubricant flow but it cannot measure the air flow and has a slow response with tens of seconds. This invention hence make it possible for a more precisely control of the lubrication process, substantially enhance the reliability, and an overall cost reduction. The sensors can also be applicable to other two phase (gas and liquid) flow measurement, monitor and control.

SUMMARY OF THE INVENTION

The invention is for integrated micro electro mechanical system (MEMS) sensors that are designed for sensing air and lubricant (oil) flow in the air/oil lubricator or lubrication machine. The MEMS sensors are micromachined on silicon substrate and packaged at the inner wall of a transportation tube or pipe in which the high speed compressed air brings the lubricant (oil) along the tube wall to the points where lubrication is required. The sensors with a response time as fast as 20 msec can sense the flow speed and the continuity of lubricant at the tube wall while provide the mass flow rate measurement of the carrier gas (compressed air). The sensor provides a programmable function for users to decide the tolerable intervals of lubricant (oil) discontinuity that requires alarm to the lubricating machine so that the lubricating points would not be dried-out by timely supply of the lubricant (oil) to the transportation tube or pipe.

The invented MEMS device contains freestanding membranes, cavities, micro channels and/or multi-layered structures. Particularly, this invention enables the measurement of the air and oil flow at the same time, which is significantly beneficial to the design and maintain the stability of the air/oil lubricator/machines. This invention also effectively solves the often-encountered slow response time and high power consumption of the current existing technology using a thermal sensor. The invention can be manufactured using a CMOS (complimentary metal-oxide-semiconductor) compatible process, thereof it provides easy manufacturability, in which can significantly reduce the cost.

For the air/oil detection, this invention measures the thermal conductivity or thermal capacity of the air or oil. The sensor can be placed at the tube or pipe wall, which can be directly measure the oil flow speed while the air flow can be calibrated against the flow rate. As the speeds of the oil/air are fast enough so that both of the measured speeds fall into the turbulence regime. When the air or oil flows in the same tube or pipe by in a well separated phase, the stability will be established only when the air/oil mass flow are equal that therefore is the very critical information of the operation of the lubricator or machines.

BRIEF DESCRIPTIONS OF THE DRAWINGS

FIG. 1—is a cross section view illustrating the schematic structure of the microelectromechanical systems (MEMS) sensor.

Figure 2:
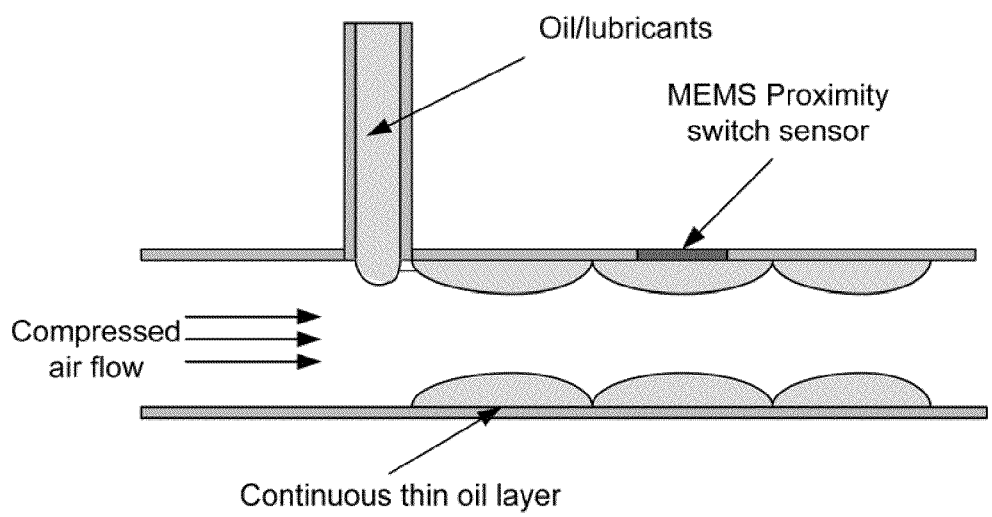

FIG. 2—is a schematic to demonstrate the application for proximity switch sensor in the oil/lubricants delivery tube system.

Figure 3:
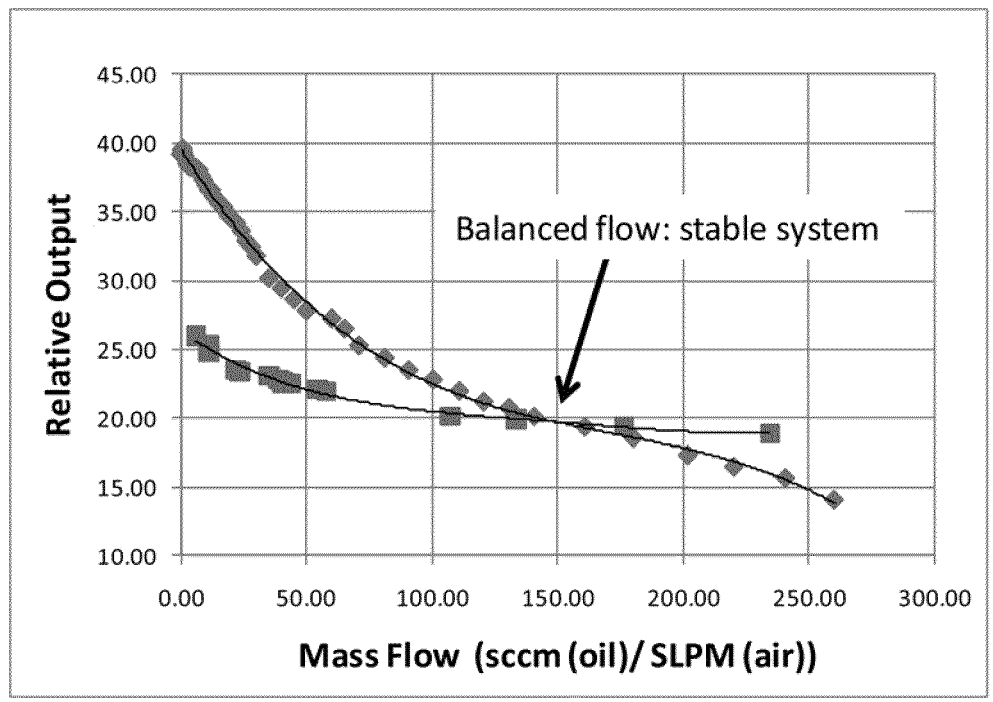

FIG. 3—An example of the measured air flow rate and oil/lubricant speed profile against the air flow rate.

Figure 4:
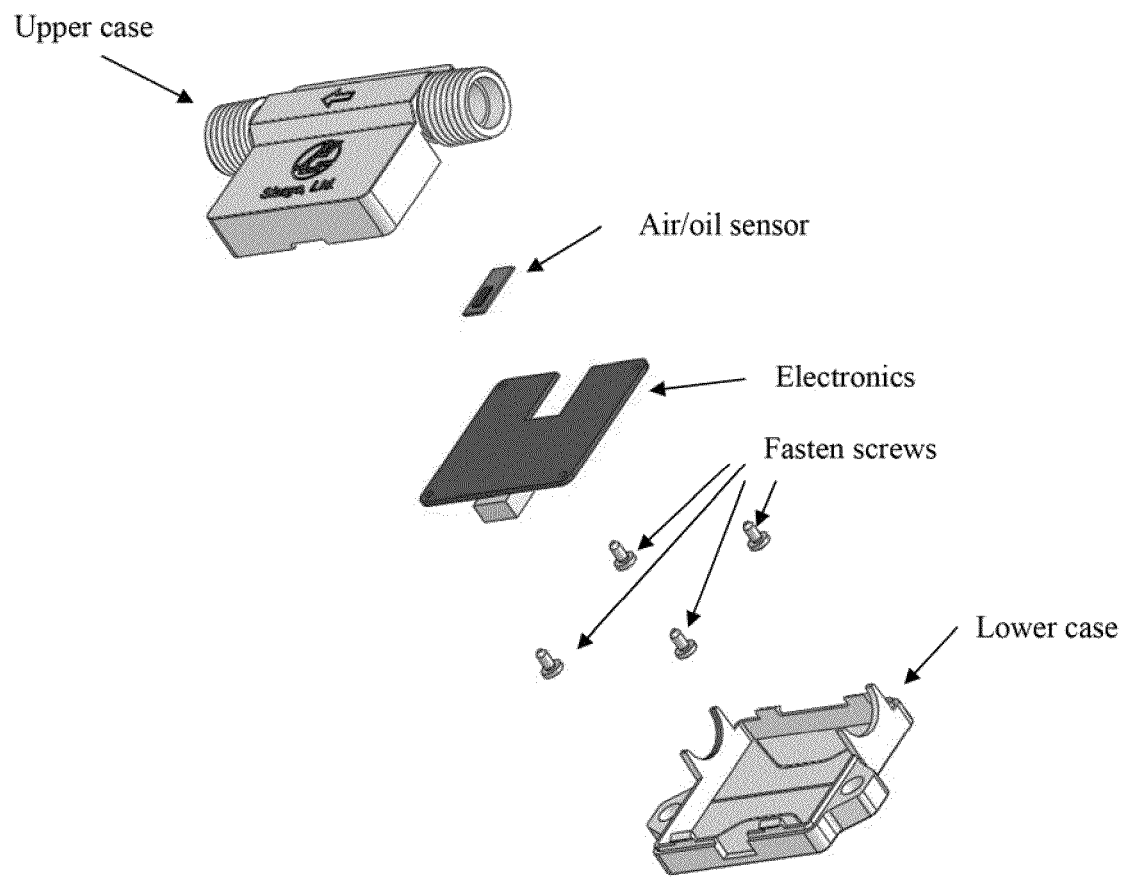

FIG. 4—is an explosive view illustrating the air/oil proximity switch sensor assembly components.

DETAILED DESCRIPTION OF THE PREFERRED EMBODIMENTS

FIG. 1 illustrates a cross section view of preferred sensor topology. The working principle behind the proximity switch sensor in air/oil lubricators is primarily based on anemometry theory. A so-called reference resistor is used to measure the ambient temperature. The ambient temperature signal will feedback to a closed-loop heater resistor control circuit. The control circuit is to keep the heater temperature constantly elevated above the ambient temperature. With the existence of media material, the heater resistor will lose heat energy to the media material either by convection or radiation, which amount is depending on the heat capacity or the flow speed of media material. Since the heater resistor is operating under constant temperature mode, therefore after losing the heat energy to media material, the feedback-controlled circuit for heater resistor has to raise its heating voltage to keep same temperature. In this way, the proximity switch sensor in air/oil lubricators can be calibrated to detect if the media composition is changed by the heating voltage, i.e. the heat dissipation rate, of the heater resistor.

The thermal dissipation rate of the heater resistor in a dynamic flow media system perceptibly depends on the flow media thermal properties which are affected by, for instance, fluid density, or the concentration of ingredients. As if the heater resistor is operating under a constant temperature mode, the power applied to keep the heater in constant temperature under various media flow could be used to detect the media situations.

In FIG. 2, for a normal operation situation, the surrounding media to the proximity sensor will be the oil lubricants. The oil lubricants will form a continuous thin layer on the sidewall of lubricants delivery tube through the compressed air flow. However, once the discontinuity of oil lubricants happens, since the surrounding media of proximity switch sensor will become air molecular solely, and thus causes the heater output voltage varied spontaneously due to the heat capacity altered by the surrounding media. The user of the sensor can setup the alarm threshold voltage depending on various flow rate combination situations of compressed air and oil/lubricants flow.

FIG. 3 is shown the chart of output signal versus the ratio of varied flow speed for air flow and oil lubricants respectively. In a balanced flow situation of stable system, the signal output will become equivalent for oil/lubricant flow and air flow.

FIG. 4 depicts a components explosive view of the complete preferred proximity switch sensor. The package of the proximity switch sensor includes one upper case and one lower case. The upper case of the package is embedded with a flow passage and a house for printed circuit board. The MEMS air/oil silicon thermal sensor, which is wire bonded on a small printed circuit board and then soldering into another electronic circuit board, is disposed on the side wall of flow passage.

While the invention has been described in terms of what are presently considered to be the most practical and preferred embodiments, it is to be understood that the invention need not be limited to the disclosed embodiment. On the contrary, it is intended to cover various modifications and similar arrangements included within the spirit and scope of the appended claims which are to be accorded with the broadest interpretation so as to encompass all such modifications and similar structures. Therefore, the above description and illustration should not be taken as limiting the scope of the present invention which is defined by the appended claims.

What is claimed is:

1. An integrated micromachining proximity switch sensor in air/oil lubricators comprising:

a micromachining silicon thermal sensor;
an assembly package embedded with an flow channel; and
an electronic, printed circuit board;
wherein said micromachining silicon thermal sensor is further comprising one heater resistor and one ambient temperature resistor; said heater resistor is disposed on a thermally isolated suspending, silicon nitride membrane extending over a cavity which is formed by bulk etching from backside of said silicon substrate;
wherein said ambient temperature resistor that is disposed on a non-membrane region of said silicon substrate, is functioned to measure ambient temperature and feedback to a heater resistor controlling circuit,
wherein said MEMS silicon thermal sensor is packaged on sidewall of said flow channel and connected to said electronic printed circuit board for controlling heating voltage of said heater resistor to be constantly elevated above ambient temperature; and
wherein said heating voltage of heater resistor is as an indication of heat dissipation rate of heater resistor corresponding to various media material; once measured said heat dissipation rate of heater resistor is abruptly lowered than a pre-set threshold value, then said electronic, printed circuit board will automatically send out an alarm signal to trigger and shut off the operation of mechanical system to avoid, oil/lubricants dry-out.

2. The integrated integrated micromachining proximity switch sensor in air/oil lubricators of claim 1 wherein
said MEMS silicon thermal sensor have a response time less than 20 msec;
therefore said proximity switch sensor is fast enough to shut off operation of said mechanical system with oil/lubricant discontinuity happened.

3. The integrated micromachining proximity switch sensor in air/oil lubricators of claim 1 wherein:
said integrated micromachining air/oil flow switch sensor by which the measured oil/lubricant discontinuity intervals can be programmed for the lubrication control in the lubrication machine for optimal lubrication process.

* * * * *